ial Patent  [19] [11] Patent Number: 4,972,829
Knerr [45] Date of Patent: Nov. 27, 1990

[54] AIR CURE BANDAGE

[76] Inventor: Richard P. Knerr, 1330 Santa Margarita, Arcadia, Calif. 91006

[21] Appl. No.: 275,769

[22] Filed: Nov. 23, 1988

[51] Int. Cl.⁵ .............................................. A61L 15/00
[52] U.S. Cl. ..................................................... 128/155
[58] Field of Search ............... 128/155, 156, 849, 850, 128/888, 889, 890, 894; 604/369

[56] References Cited

U.S. PATENT DOCUMENTS

| | | | |
|---|---|---|---|
| 1,229,633 | 6/1972 | Manning | 128/888 X |
| 2,807,262 | 9/1957 | Lew . | |
| 3,234,941 | 2/1966 | Tucker | 128/888 |
| 3,658,065 | 4/1972 | Hirsch | 128/156 |
| 3,677,266 | 7/1972 | Green | 128/849 |
| 3,782,378 | 1/1974 | Page | 128/888 |
| 3,888,248 | 6/1975 | Moore . | |
| 3,927,669 | 12/1975 | Glatt . | |
| 3,976,066 | 8/1976 | McCartney | 128/889 |
| 4,231,357 | 11/1980 | Hessner . | |
| 4,360,015 | 11/1982 | Mayer . | |
| 4,561,435 | 12/1985 | McKnight . | |
| 4,566,458 | 1/1986 | Weinberg | 128/890 X |
| 4,667,666 | 5/1987 | Fryslie . | |
| 4,675,009 | 6/1987 | Hymes et al. . | |
| 4,848,329 | 7/1989 | Dardik | 128/888 X |

Primary Examiner—Alan Cannon
Assistant Examiner—N. Paul
Attorney, Agent, or Firm—Christie, Parker & Hale

[57] ABSTRACT

A protective bandage is provided having a circumferentially shaped foam base topped with a protective grill or screen. The grill is attached to the foam base either mechanically or with an adhesive bonding sheet. The underside of the foam base is coated with an adhesive for attachment to the skin.

The resulting bandage provides protection from physical trauma, enhances the flow of air to the wound, and allows application of medication to the wound without the need for bandage removal.

19 Claims, 8 Drawing Sheets

AIR CURE BANDAGE

BACKGROUND OF THE INVENTION

The present invention relates to a flexible, protective device for cuts, abrasions, lesions, and other types of wounds. The medical art has commonly responded to the need for protective coverings for cuts, wounds and the like through the direct attachment of sterile pads and gauze to the wound, with adhesive fasteners. Examples are shown in Moore et al. (U.S. Pat. No. 4,360,015) and Glatt (U.S. Pat. No. 3,927,669). Such devices serve to absorb wound discharges, and protect the wound from entry of foreign matter and protection. Optionally, a medicament may be contained within the pad and released to the wound over time, as shown in Hymes et al., (U.S. Pat. No. 4,675,009).

Such devices suffer from the problem that, as blood, pus, serum and other wound discharges coagulate, a scab is formed, often within the matrix of the "protective" gauze pad. Removal of the pad causes the scab to be pulled away from the wound, and the healing process is disrupted. The problem is sometimes compounded by the need to remove the bandage in order to apply new medication. Additionally, such devices have the drawback of depressing the beneficial flow of air to the wound; oxygen is particularly important in aiding the healing process. Finally, these devices provide only minimal protection for the wound from physical trauma. Inadvertent contact with the covered wound area often results in additional injury to the wound.

Attempts at elevating the protective covering over the wound have provided limited results. Typically, the wound is "capped" by a dome-shaped covering which circumscribes, but does not directly contact the wound, the covering being held in place by adhesive strips. Examples are shown in Fryslie (U.S. Pat. No. 4,667,666).

Unfortunately, while premature scab disruption is avoided, new problems are created. The elevated domed covering tends to admit and harbor bacteria; instead of facilitating wound healing, a "greenhouse effect" is created, and infection results. Such domed bandages also suffer from a lack of absorbency. The materials of construction necessary for providing the domed covering with structural integrity afford little absorbency of wound discharges. Moreover, devices as shown in Fryslie are not easily manufactured by common techniques.

Accordingly, a need exists for a new protective bandage for wounds that eliminates premature scab disruption, allows easy application of medication to the wound without removal of the bandage, maximizes air flow to the wound, and provides substantial protection from physical trauma, without a bacteria-harboring "greenhouse effect." Fulfilling this need is the object of the invention.

SUMMARY OF THE INVENTION

The present invention comprises a flexible disposable bandage of multi-layer construction for use with abrasions, cuts, open ulcerations, and other types of wounds. In the following paragraphs, the invention is described as being attached to the body, to the skin, etc. The invention is not limited to protecting the human body; rather, the bandage works equally well on animals having wounds, cuts and abrasions. Henceforth, whenever a wound region is described, it is to be understood that both human and animal wounds are being referred to. The word "skin" refers to flesh, whether covered with hair or fur or not.

More specifically, a flexible, yet structurally firm, pad of porous foam, having a circumferential design, forms the base of the bandage. The foam pad is readily formable, and may be bent into contoured or compound shapes, as required by the location of the wound. A semirigid metal or plastic protective grill or screen, having an area slightly larger than the inner region defined by the circumferential design of the foam base, is attached to the upper face of the foam base with an adhesive bonding sheet. In alternate embodiments the grill is mechanically attached to the foam base, obviating the need for an adhesive bonding sheet. An adhesive coating on the lower face of the base provides means for attaching the bandage to the skin. A removable sheet covers the adhesive coating until the bandage is to be applied to the wound. The circumferential design of the bandage allows additional attachment means (i.e., adhesive tape) to be utilized to further secure the bandage to the skin.

As an optional embodiment of the invention, contained therein, a gauze sheet, with or without a medicament, is placed over the protective grill and bonding material, providing additional protection from dirt and debris.

As yet another embodiment of the invention, the foam base comprises two or more parts: an inner circumferential portion consists of an absorbent material, and an outer circumferential portion consists of a flexible, yet structurally firm foam material. If desired, a medicament may be contained within the absorbent material portion of the base.

In operation, the removable sheet is removed from the lower face of the foam base, exposing the adhesive coating. The bandage is then placed over and around the wound area, so that the foam base circumscribes the wound. The adhesive on the lower face of the foam base affixes the bandage to the skin surrounding the wound. If desired, the bandage can be further secured with the use of adhesive tape.

The circumferential design of the bandage, and the grill provide substantial protection from traumatic contact between the wound and external objects. The height and cross-sectional width of the foam base provide structural integrity and prevent significant compression, or flattening, of the bandage due to contact with an external object, thereby preventing direct pressure against the wound. Pads of varying thickness may be used, depending on the location of the wound and/or the type and size of the region being protected by the bandage.

In one embodiment of the invention, a bandage of variable height is provided by constructing the foam base as a series of stacked layers. Each layer is adhesively attached to the next layer, and is peelably removable therefrom. Thicker bandages are obtainable by stacking multiple layers of foam atop one another. Thus variable bandage height and protectiveness is realizable. Color-coding the layers provides ready recognition of the height of a given configuration.

Because the top face of the bandage consists of a grill or screen and is substantially open, medicaments or cleaning salves, such as hydrogen peroxide, may be poured directly onto the wound area, obviating the need for removal of the bandage.

The bandage is adaptable for use on appendages by replacing the foam base with at least one foam ring, on which is mounted a generally cylindrical protective grill. Thus, a finger wound can be protected in a manner similar to that described above.

These and other advantages of the invention can be more clearly understood by reference to the drawings.

DETAILED DESCRIPTION OF THE INVENTION

The present invention relates to a protective bandage for wounds that provides protection from physical trauma while simultaneously allowing maximum exposure to air, thereby enhancing the wound healing process.

Figure 1:
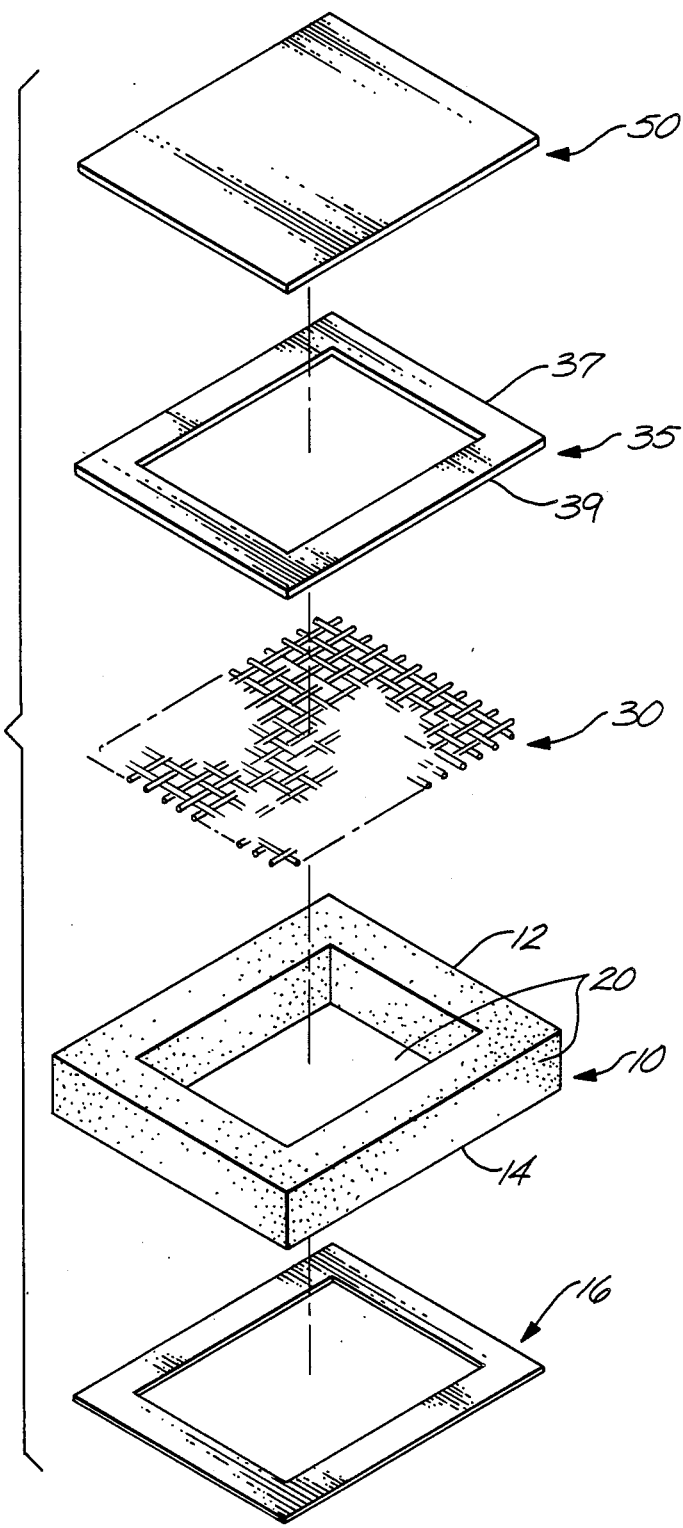
FIG. 1 is an exploded view of the invention.

Referring to FIG. 1, a bandage 1 is shown in exploded perspective, and has a circumferential foam base 10 topped by a grill 30, that is secured to the base with a bonding sheet 35. An optional gauze sheet 50 may be further attached to the upper face 37 of the bonding sheet 35.

The foam base 10 has an upper face 12 and a lower face 14, and defines, circumferentially, an inner region 20, wherein the wound to be protected (not shown) is located.

Figure 12:
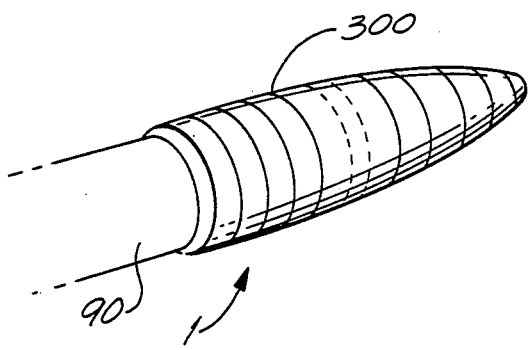
FIG. 12 is a perspective view of yet another embodiment of the invention.
Figure 13:
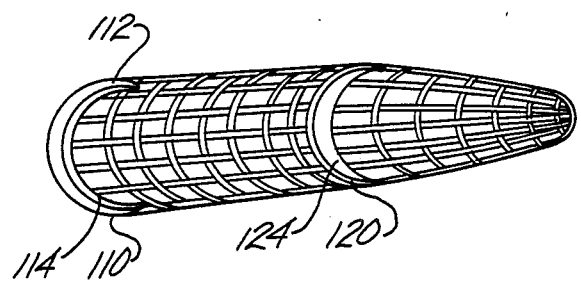
FIG. 13 is a cut-away view of the embodiment shown in FIG. 12.
Figure 14:
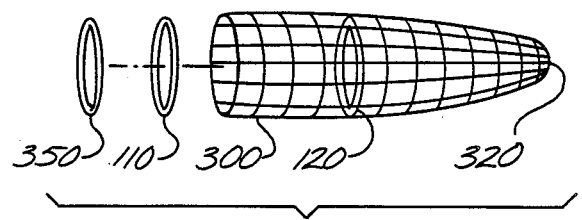
FIG. 14 is an exploded view of the embodiment shown in FIG. 12.

As used herein, the word "circumferential" is given its broadest possible meaning, i.e., "of or pertaining to an enclosure." All manner of foam bases of predetermined geometric shape and thickness, capable of enclosing a predetermined area, may be utilized. For example, the embodiment depicted in FIG. 1 has a rectangular, "frame-like" foam base 10 that encloses an inner area 20. FIGS. 12–14 show a bandage in which foam rings are used. Other "circumferential" shapes are contemplated.

The lower face 14 of the foam base 10 is coated with an adhesive (not shown), providing preferred means for securing the bandage 1 to the skin. A removable sheet 16, of glassine, cellophane or similar material, adheres to the adhesive coating until the bandage is applied. By peeling away the sheet 16, the adhesive coating is exposed, and the bandage 1 can then be attached to the skin. In an alternate embodiment of the invention, the bandage is further secured to the skin with supplementary attachment means, such as adhesive tape (not shown) applied to the skin and the bandage.

Figure 6:
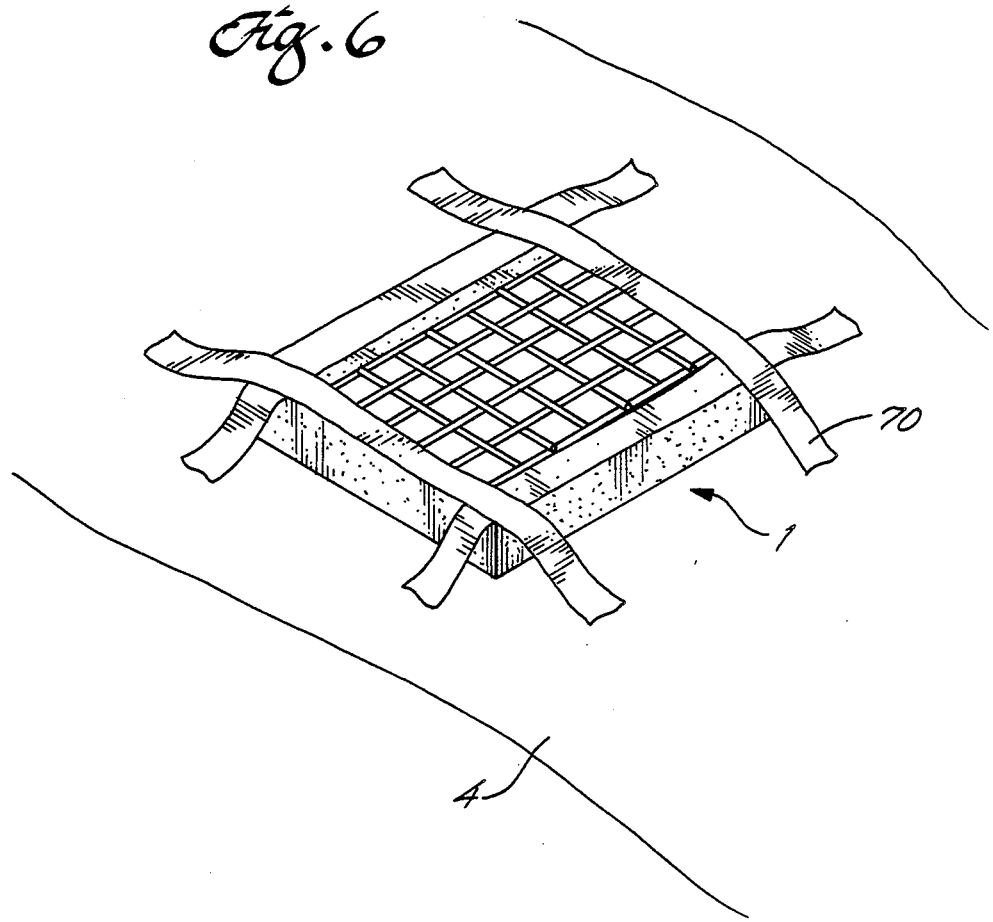
FIG. 6 is a perspective view of the invention with supplementary attachment means.

In another embodiment of the invention, the lower face 14 of the foam base is not coated with adhesive, and the bandage is secured to the skin with other attachment means. FIG. 6 shows such an embodiment of the invention in which an adhesive tape 70 is attached to the periphery of the bandage 1 and the surrounding skin 4.

A grill, or screen, 30 lies situate over the inner region 20 of the foam base 10, and makes direct contact with the upper face 12 of the base. The grill 30 may be constructed of metal or plastic wires arranged in a lattice configuration. In a preferred embodiment, the area of the grill 30 is slightly greater than the area of the inner region 20, and slightly less than the area defined by the outer perimeter of the foam base.

A bonding sheet 35, of suitable adhesive material, having an upper face 37 and a lower face 39, is placed directly over the grill, or screen, 30, and secures the grill 30 firmly against the upper face 12 of the foam base 10. Preferably, the circumferential dimensions of the bonding sheet 35 are identical to those of the foam base 10, so that optimum adhesion between the bonding sheet 35 and the foam base 10 occurs. In alternate embodiments shown in FIGS. 7-10 the grill 30 is secured to the foam base 10 by mechanical means with some portion of the grill embedded in the foam base.

Figure 7:
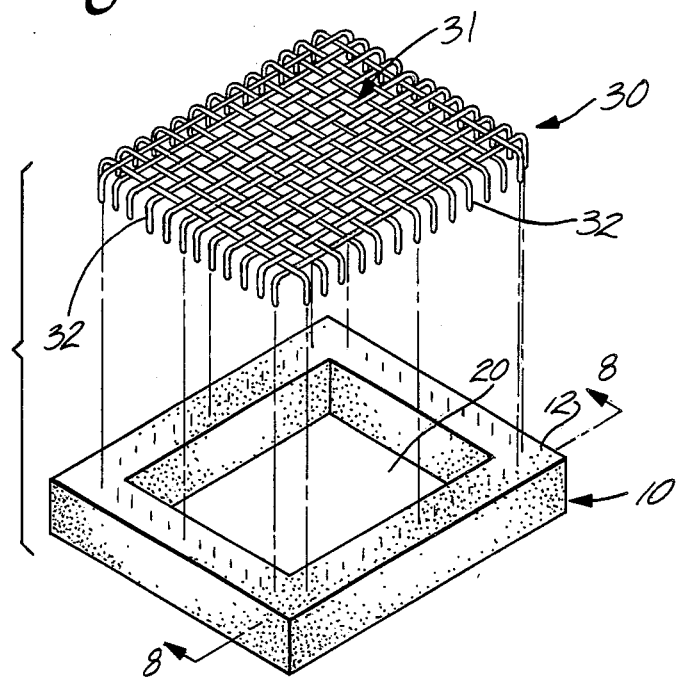
FIG. 7 is an exploded view of another embodiment of the invention.
Figure 8:
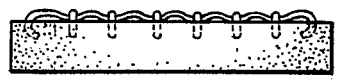
FIG. 8 is a cross-section taken on line 7—7 of FIG. 7, after crimping.

FIG. 7 shows an exploded view of one such embodiment. Grill 30 comprises a generally planar central region 31 peripherally encompassed by downwardly extending tines 32. The tines 32 are embedded into the upper face 12 of the foam base 10. By mechanically crimping the periphery of the bandage, the tines 32 are physically secured to the foam base 10, in much the same way as a staple works. A cross-sectional view of such a bandage is shown in FIG. 8. If desired, additional attachment means such as adhesive tape can further secure the grill 30 to the foam base 10.

Figure 9:
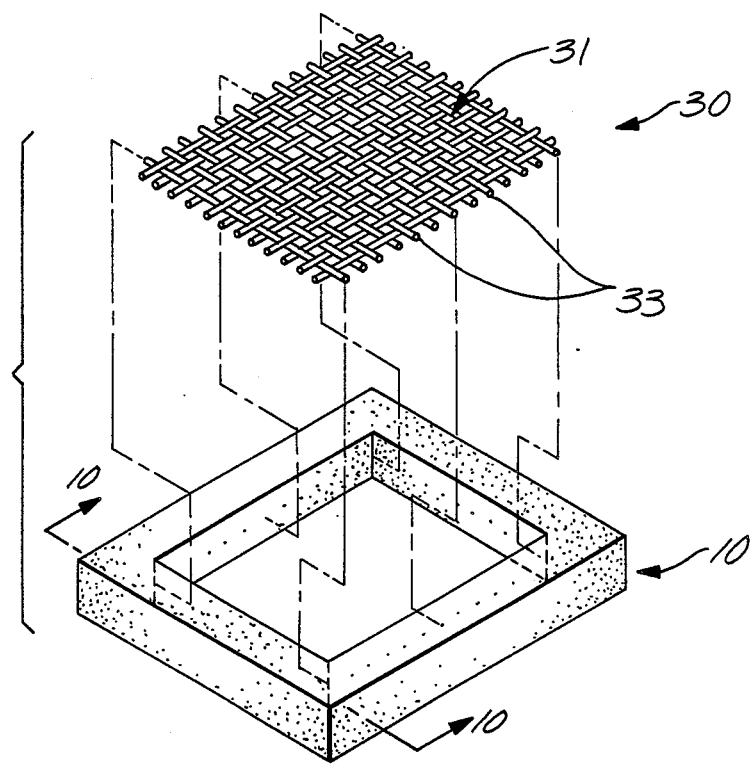
FIG. 9 is an exploded view of yet another embodiment of the invention.
Figure 10:
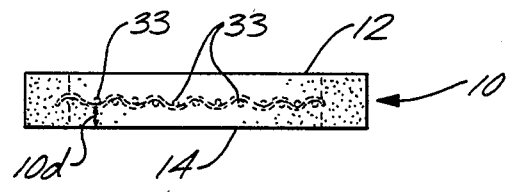
FIG. 10 is a cross-section taken on line 9—9 of FIG. 9.

In FIGS. 9 and 10, another embodiment is shown in which the protective grill is mechanically attached to the foam base. Grill 30 comprises a generally planar central region 31 and a circumferential region of exposed ends 33. The ends 33 of the grill 30 engage the interior of the foam base 10 as shown. As indicated in the cross-sectional view shown in FIG. 10, the ends 33 are directly embedded in the foam base 10, such that the grill 30 is located a distance 10d above the lower face 14 of the foam base 10. Thus, the grill 30 is elevated above the wound (not shown).

In another embodiment of the invention (not shown), the foam base 10 comprises a series of stacked layers of foam, each layer having the same circumferential design as the other bases. At least one side of each layer is coated with an adhesive, and thus a bandage of variable height can be constructed, wherein each foam layer is adhesively attached to another layer, and peelably removable therefrom. Thus, a "thicker", more protective bandage is realizable. The individual layers may be color-coded to provide ready recognition of the thickness of a given configuration.

Figure 2:
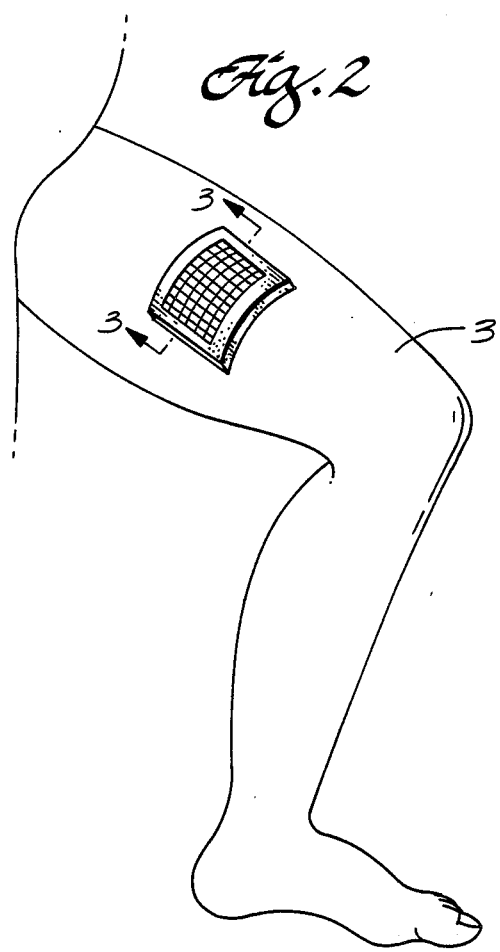
FIG. 2 is a perspective view of the invention affixed to a human limb.

Referring now to FIG. 2, a bandage is shown affixed to a human limb 3. It will be noted that the shape of the bandage 1 is no longer "flat", but rather conforms to the curvature of the leg, because of the flexibility of the foam base 10. This is more readily apparent with reference to FIGS. 3 and 11.

Figure 3:
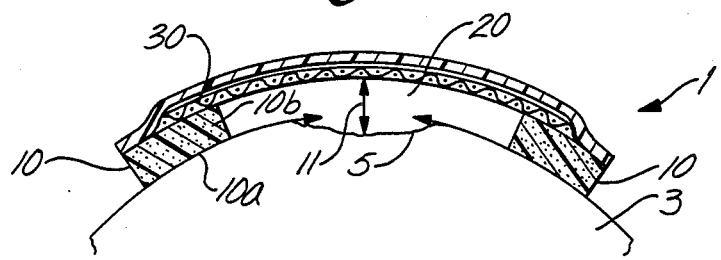
FIG. 3 is a cross-section taken on line 2—2 of FIG. 2.

As viewed along line 2—2 of FIG. 2, FIG. 3 shows a cross-section of the bandage 1 affixed to a human 3, and protecting a wound 5. The foam base 10 has a cross-sectional width 10a and a height 10b. As described above, an inner region 20 is defined by the circumferential design of the foam base 10.

The inner region 20 has a height 11 defined by the normal distance between the wound 5 and the grill 30.

The values of the dimensions of the foam base—width 10a, height 10b, and the area of the inner region 20—determine the height 11 of the grill 30 over the wound 5.

Figure 11:
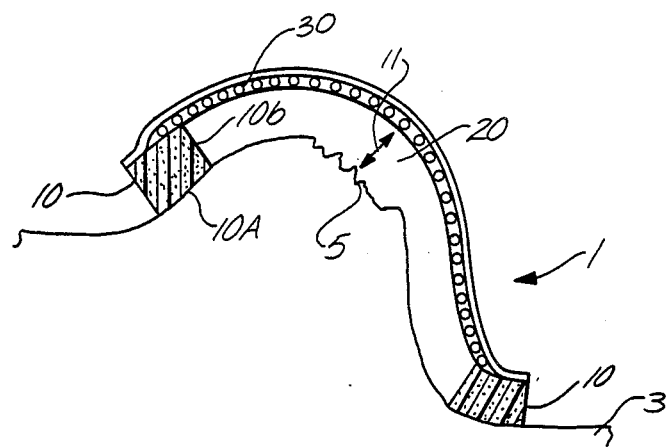
FIG. 11 is a sectional view of the invention.

A wound 5 of large area necessarily must be contained within an inner region 20 of correspondingly large area. Proper choice of the dimensions of the foam base depends on the size and location of the wound, as the bandage may be affixed to wound regions having compound curves as shown in FIG. 11.

Figure 4:
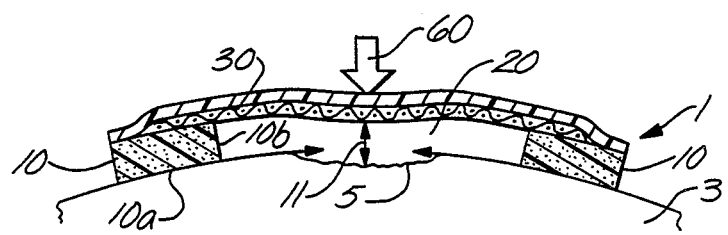
FIG. 4 is a schematic cross-sectional view similar to FIG. 3, showing an external force applied to the bandage.

With reference to FIG. 4, a bandage 1 is affixed to a limb 3, and protects a wound 5. The bandage is subjected to a force 60 that is applied in a direction normal to the surface of the wound.

The force 60 causes the grill 30 to deflect toward the wound 5, resulting in a contraction of the height 11 of the grill over the wound. The structural integrity of the foam base 10, however, prevents the grill 30 from actually contacting the wound. By carefully choosing the dimensions of cross-sectional width 10a and height 10b of the foam base 10, in accordance with the area of the inner region 20, physical trauma to the wound 5 can be prevented, should an external force 60 be applied.

Figure 5:
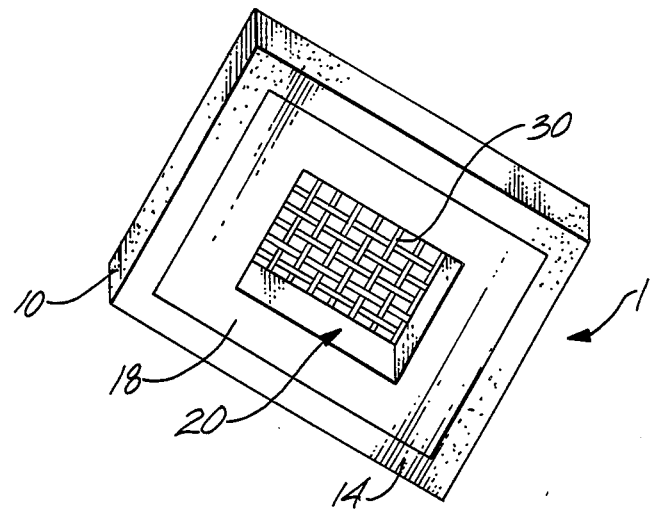
FIG. 5 is an alternate embodiment of the invention.

Referring now to FIG. 5, an alternate embodiment of the bandage 1 is shown, in which an inset 18 of absorbent material is circumscribed by the foam base 10. The inset 18 may be composed of gauze or other suitably absorbent material, and may contain a medicament. Wound discharge, such as blood, pus, or serum, is absorbed by the inset 18. The inset 18 is secured to the foam base 10 by attachment means (not shown). The lower face 14 of the foam base 10 is coated with an adhesive (not shown) providing means for attaching the bandage 1 to the skin.

In another embodiment of the invention the bandage is adapted to protect wounds on fingers and other appendages. The bandage is generally cylindrical in shape and comprises at least one foam ring for elevating a protective grill or screen above the wound.

As shown in FIGS. 12-14, a first foam ring 110 and a second foam ring 120 support a protective grill or screen 300 an elevated distance away from the finger 90 and/or the wound (not shown). That is, the finger or appendage is inserted through the foam rings. The inner surface 114 of first foam ring 110 may be coated with an adhesive (not shown) for affixing the bandage 1 to the finger 20. Second foam ring 120 also has an inner surface 124 which may or may not be coated with an adhesive.

The grill 300 is generally cylindrical, and has an open end 310 and a closed end 320. The grill 300 is attached to the foam rings 110 and 120 by a manner similar to that described above. In the embodiment shown in FIGS. 12-14, grill 300 is attached to first foam ring 110 with an adhesive bonding ring 350. If desired, the grill 300 may also be affixed to second foam ring 120 with an adhesive bonding ring (not shown). The bandage functions in a manner similar to that described above.

The above embodiments are offered as preferred and illustrative concepts of the invention; other arrangements may be foreseeable to those skilled in the art, without departing from the spirit and scope of the invention, which is to be limited only by the following claims:

What is claimed is:

1. A protective apparatus for promoting healing of a wound, comprising:
    a frame-like foam base enclosing an inner region of predetermined geometric shape, said frame having an upper face, a lower face, and a predetermined thickness sufficient to create an enclosure of a predetermined volume surrounding the wound on all sides;
    a grill comprising a network of more than two crossed tines defining a plurality of openings, attached to the upper face of the foam base and disposed over the inner region;
    means for attaching the grill to said upper face; and
    means for attaching the foam base around a wound, whereby flow of air into the enclosure surrounding the wound is facilitated.

2. The apparatus as claimed in claim 1, wherein the grill is constructed of a semi-rigid material.

3. The apparatus as claimed in claim 2, wherein the means for attaching the grill to the upper face of the foam base comprises an adhesive material.

4. The apparatus as claimed in claim 3, wherein the adhesive material comprises a bonding sheet of a shape similar to the foam base such that the grill is disposed between the bonding sheet and the upper face of the foam base.

5. The apparatus as claimed in claim 4, wherein the means for attaching the foam base around a wound comprises an adhesive coating on at least some portion of the lower face of the foam base.

6. The apparatus as claimed in claim 5, further comprising means for absorbing wound discharge.

7. The apparatus as claimed in claim 6, wherein the means for absorbing wound discharge comprises:
    an absorbent inset of a predetermined shape surrounded by the foam base; and
    means for attaching the inset to the foam base.

8. The apparatus as claimed in claim 7, wherein the means for attaching the absorbent inset to the foam base comprises an adhesive material.

9. The apparatus as claimed in claim 6, further comprising:
    an air permeable covering and means for attaching the covering to the grill.

10. The apparatus as claimed in claim 9, wherein the means for attaching the covering to the grill comprises an adhesive material.

11. The apparatus as claimed in claim 1, wherein the means for attaching the grill to the upper face of the foam base is mechanical.

12. An apparatus for protecting a wound on an appendage of a human or animal, comprising:
    at least one foam ring through which an appendage can be inserted, each foam ring having an inner surface, an outer surface and a predetermined thickness;
    a generally cylindrical grill having an open end and a closed end and defining a plurality of openings attached to the outer surface of each foam ring, the grill and foam ring cooperating to form an enclosure of a predetermined volume surrounding the wound on all sides and to space the grill a predetermined distance away from the appendage;

means for attaching the grill to the outer surface of each foam ring; and means for attaching each foam ring to said appendage, whereby flow of air to the wound is facilitated.

13. The apparatus as claimed in claim 12, wherein the grill is constructed of a semi-rigid material.

14. The apparatus as claimed in claim 13, wherein the means for attaching the grill to the outer surface of each foam ring is an adhesive material.

15. The apparatus as claimed in claim 14, wherein the adhesive material comprises a bonding ring overlying the grill, such that the grill is secured between the bonding ring and the outer surface of the foam ring.

16. The apparatus as claimed in claim 15, wherein the means for attaching each foam ring to an appendage comprises an adhesive coating on the inner surface of the ring.

17. The apparatus as claimed in claim 16, further comprising means for absorbing wound discharge.

18. The apparatus as claimed in either claim 11 or claim 16, further comprising:

an air permeable covering and means for attaching said covering to the grill.

19. The apparatus as claimed in claim 18, wherein the means for attaching is an adhesive material.

* * * * *

UNITED STATES PATENT AND TRADEMARK OFFICE
CERTIFICATE OF CORRECTION

PATENT NO. : 4,972,829
DATED : November 27, 1990
INVENTOR(S) : Richard P. Knerr

It is certified that error appears in the above-identified patent and that said Letters Patent is hereby corrected as shown below:

Column 1, line 17, after "al." delete the comma.
Column 1, lines 53,54, change "air flow" to -- airflow --.
Column 1, line 61, change "multi-layer" to -- multilayer --.

Column 3, lines 13,22,26, change "cross-section" to -- cross section -- (all occurrences).
Column 3, line 13, change "line 2--2" to -- line 3--3 --.
Column 3, line 22, change "line 7--7" to -- line 8--8 --.
Column 3, line 26, change "line 9--9" to -- line 10--10 --.

Column 4, line 12, delete the commas after both "grill" and "screen".
Column 4, line 21, delete the commas after both "grill" and "screen".

Column 5, line 2, change "cross-section" to -- cross section --.
Column 5, line 2, after "human" insert -- limb --.
Column 5, line 60, change "by" to -- in --.

UNITED STATES PATENT AND TRADEMARK OFFICE
CERTIFICATE OF CORRECTION

PATENT NO. : 4,972,829

DATED : November 27, 1990

INVENTOR(S) : Richard P. Knerr

It is certified that error appears in the above-identified patent and that said Letters Patent is hereby corrected as shown below:

In the Claims

Column 6, line 23, change "semi-rigid" to -- semirigid --.

Column 7, line 9, change "semi-rigid" to -- semirigid --.

Signed and Sealed this

Twenty-first Day of July, 1992

Attest:

DOUGLAS B. COMER

Attesting Officer

Acting Commissioner of Patents and Trademarks